US012746087B2

(12) United States Patent
McClure et al.

(10) Patent No.: US 12,746,087 B2
(45) Date of Patent: Sep. 29, 2026

(54) DUAL PURPOSE PACKAGING FOR BIOPSY DEVICE

(71) Applicant: Devicor Medical Products, Inc., Cincinnati, OH (US)

(72) Inventors: Jeffrey McClure, Lebanon, OH (US); Jake Schubert, Bellevue, KY (US)

(73) Assignee: Devicor Medical Products, Inc., Cincinnati, OH (US)

( * ) Notice: Subject to any disclaimer, the term of this patent is extended or adjusted under 35 U.S.C. 154(b) by 820 days.

(21) Appl. No.: 18/128,398

(22) Filed: Mar. 30, 2023

(65) Prior Publication Data

US 2023/0329821 A1 Oct. 19, 2023

Related U.S. Application Data

(60) Provisional application No. 63/332,462, filed on Apr. 19, 2022.

(51) Int. Cl.
*A61B 50/36* (2016.01)
*A61B 10/02* (2006.01)

(52) U.S. Cl.
CPC .............. *A61B 50/36* (2016.02); *A61B 10/02* (2013.01)

(58) Field of Classification Search
CPC ................................ A61B 50/36; A61B 10/02
USPC .................................................. 206/363, 370
See application file for complete search history.

(56) References Cited

U.S. PATENT DOCUMENTS 5,545,121 A * 8/1996 Yabe .................. A61B 1/00142 206/363
6,090,073 A * 7/2000 Gill ..................... A61J 15/0069 604/164.01
2008/0043905 A1* 2/2008 Hassanpourgol .... A61B 6/0435 606/130
2014/0353189 A1* 12/2014 Lotosky-Compton ...................... A61B 46/23 206/370
2021/0106309 A1* 4/2021 Mesaros .............. A61B 8/4405
2021/0186641 A1* 6/2021 Cummings ............ A61B 50/33

* cited by examiner

*Primary Examiner* — Jacob K Ackun
(74) *Attorney, Agent, or Firm* — FBT Gibbons LLP

(57) ABSTRACT

A system for maintaining sterility during a biopsy procedure includes a cart, a packaging assembly, and a biopsy probe. The cart includes a support member defining an open inner portion and an opening in communication with the open inner portion. The packaging assembly has a container tray and a retainer tray. The packing assembly is configured to receive the biopsy probe. The open inner portion of the support member is configured to engage a portion of both the container tray and the retainer tray simultaneously to hold the container tray and the retainer tray within the open inner portion of the support member to thereby provide a sterile work surface during the biopsy procedure.

19 Claims, 12 Drawing Sheets

DUAL PURPOSE PACKAGING FOR BIOPSY DEVICE

PRIORITY

This application claims priority to U.S. Provisional Application Ser. No. 63/332,462, entitled "Dual Purpose Packaging for Biopsy Device," filed on Apr. 19, 2022, the disclosure of which is incorporated by reference herein.

BACKGROUND

A biopsy is the removal of a tissue sample from a patient to enable examination of the tissue for signs of cancer or other disorders. Tissue samples may be obtained in a variety of ways using various medical procedures involving a variety of the sample collection devices. For example, biopsies may be open procedures (surgically removing tissue after creating an incision) or percutaneous procedures (e.g. by fine needle aspiration, core needle biopsy, or vacuum assisted biopsy). After the tissue sample is collected, the tissue sample may be analyzed at a lab (e.g. a pathology lab, biomedical lab, etc.) that is set up to perform the appropriate tests (such as histological).

Biopsy samples have been obtained in a variety of ways in various medical procedures including open and percutaneous methods using a variety of devices. For instance, some biopsy devices may be fully operable by an operator using a single hand, and with a single insertion, to capture one or more biopsy samples from a patient. In addition, some biopsy devices may be tethered to a vacuum module and/or control module, such as for communication of fluids (e.g., pressurized air, saline, atmospheric air, vacuum, etc.), for communication of power, and/or for communication of commands and the like. Other biopsy devices may be fully or at least partially operable without being tethered or otherwise connected with another device.

Regardless of the particular mode of obtaining a biopsy samples, maintaining sterility within a procedure room during a biopsy procedure is generally desirable. One element to maintaining sterility may be to maintain a sterile work surface within the procedure room. Such a sterile work surface may be desirable to promote the segregation of instruments and other tools used during a biopsy procedure between sterile and non-sterile areas of the procedure room.

In some circumstances, a sterile work surface may be maintained within a biopsy procedure room by use of a Mayo tray stand in combination with other elements such as sterile drapes, towels, and/or etc. For instance, a sterile drape may be applied over the upper surface of the Mayo tray stand to provide the sterile work surface. Various sterile instruments or other tools may be then be place on the sterile work surface during the biopsy procedure to maintain sterility of such sterile instruments or other tools when not in use during the biopsy procedure. Although this technique for maintaining a sterile work surface may be effective, the technique may require additional setup steps. It also may generate additional waste due to the use of sterile drapes, towels, and/or etc. The use of a Mayo tray stand in combination with other elements to maintain a sterile work surface may accordingly be undesirable in some contexts.

While several systems and methods have been made and used for obtaining and processing a biopsy sample, it is believed that no one prior to the inventor has made or used the invention described in the appended claims.

BRIEF DESCRIPTION OF THE DRAWINGS

It is believed the present invention will be better understood from the following description of certain examples taken in conjunction with the accompanying drawings, in which like reference numerals identify the same elements and in which.

Figure 1:
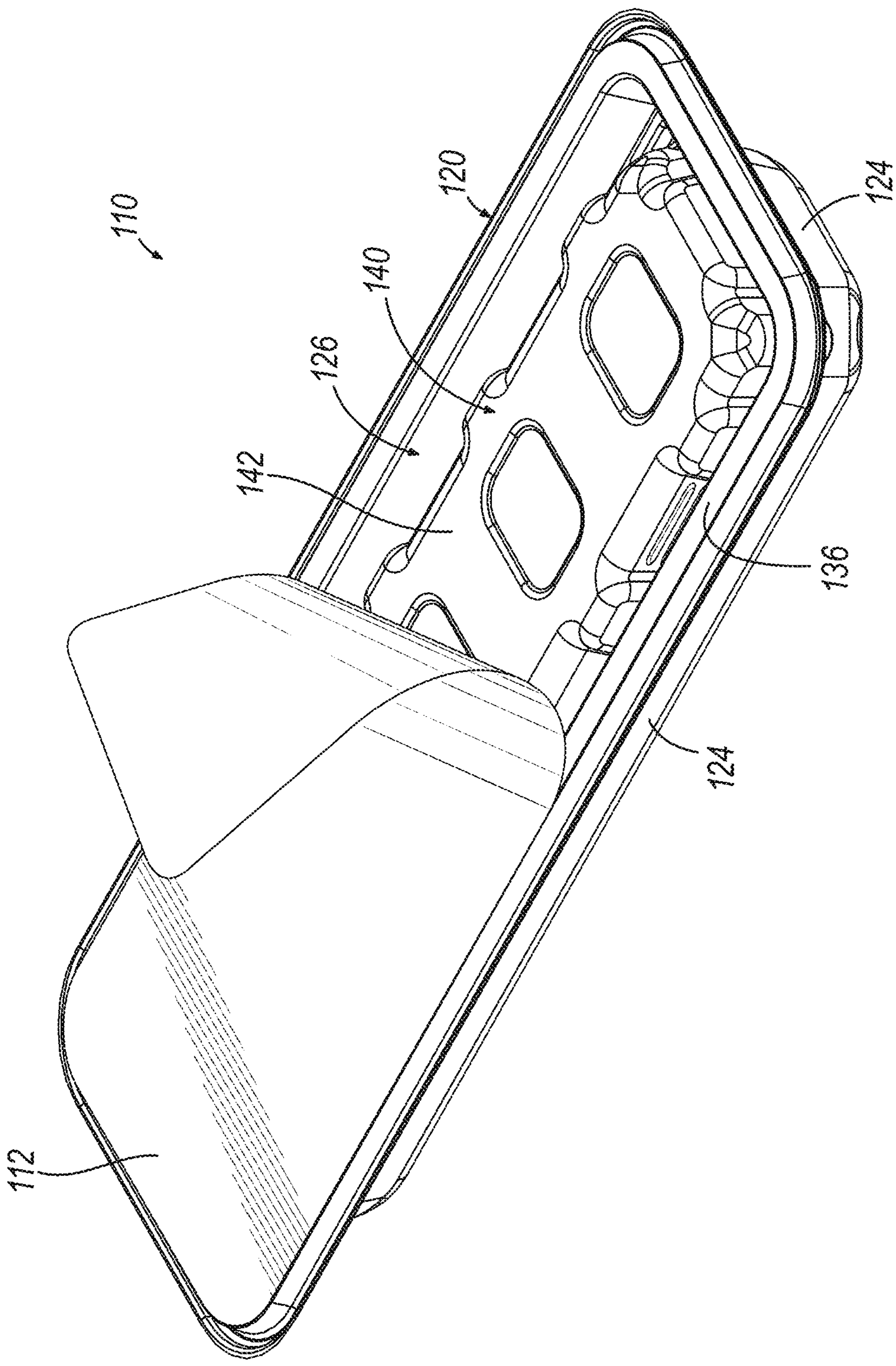
FIG. 1 depicts a perspective view of an example of a sterile dual-purpose packaging assembly for use in a biopsy procedure.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION OF THE INVENTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

I. Example of Dual-Purpose Packaging

Sterile packaging assemblies may be used in a variety of contexts to preserve the sterility of instruments until a procedure is performed. In some circumstances, packaging assemblies may be used only for the purpose of transport and then discarded at the beginning of a procedure once the instruments contained therein are removed. Sterility of such instruments may then be maintained by other procedure room equipment. One example of such procedure room requirements may be a Mayo tray stand with one or more sterile drapes disposed on a surface of the Mayo tray stand.

The draped Mayo tray stand configuration described above may be desirable in some circumstances because both sterile drapes and Mayo tray stands are readily available in clinical environments. However, in other circumstances such a configuration may be undesirable because of additional time required to acquire both components, additional time to set up the configuration, and disposal/reuse of the components as appropriate. Such a configuration may also be undesirable due to increased waste associated with disposal of sterile drapes. It may accordingly be desirable in some circumstances to eliminate additional equipment such as sterile drapes and Mayo tray stands and instead use components more closely aligned with a given procedure for the purpose of maintaining sterility both before and during the procedure.

FIG. 1 shows an example of a sterile dual-purpose packaging assembly (110). In the present version, packaging assembly (110) is generally configured as a sterile container for a biopsy device, accessory components for use with the biopsy device and/or other tools for use in a biopsy procedure. Packaging assembly (110) of the present version includes a container tray (120) (also referred to as a primary tray, base tray, main tray, or container), a retainer tray (140) (also referred to as a secondary tray, retainer, or holder), and a sterile barrier (112). Retainer tray (140) is configured to nest within container tray (120) to add structural stability to packaging assembly (110) and to maintain the contents of packaging assembly (110) in a predetermined position within container tray (120). Meanwhile, sterile barrier (112) is configured to seal packing assembly (110), thereby creating a sterile barrier between the interior of packing assembly (110) and the exterior of packaging assembly (110). In some versions, sterile barrier (112) may include a variety of materials such as paper composites, polymers, and/or etc. Additionally, sterile barrier (112) may be removably adhered to an upper portion of container tray (120) for ease of removal prior to a biopsy procedure.

Figure 2:
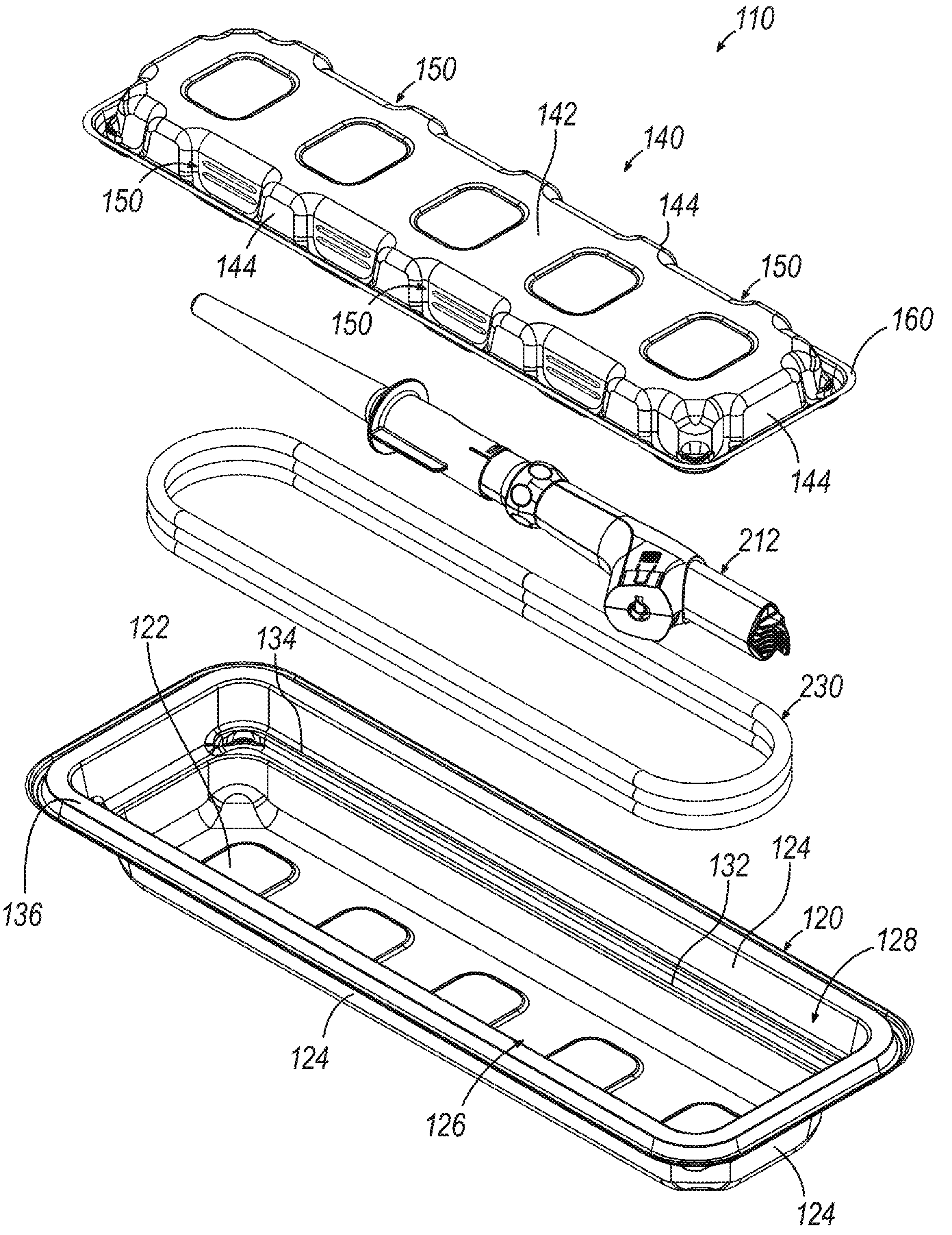
FIG. 2 depicts an exploded perspective view of the packaging assembly of FIG. 1, the packaging assembly containing a biopsy probe and tube set.
Figure 3:
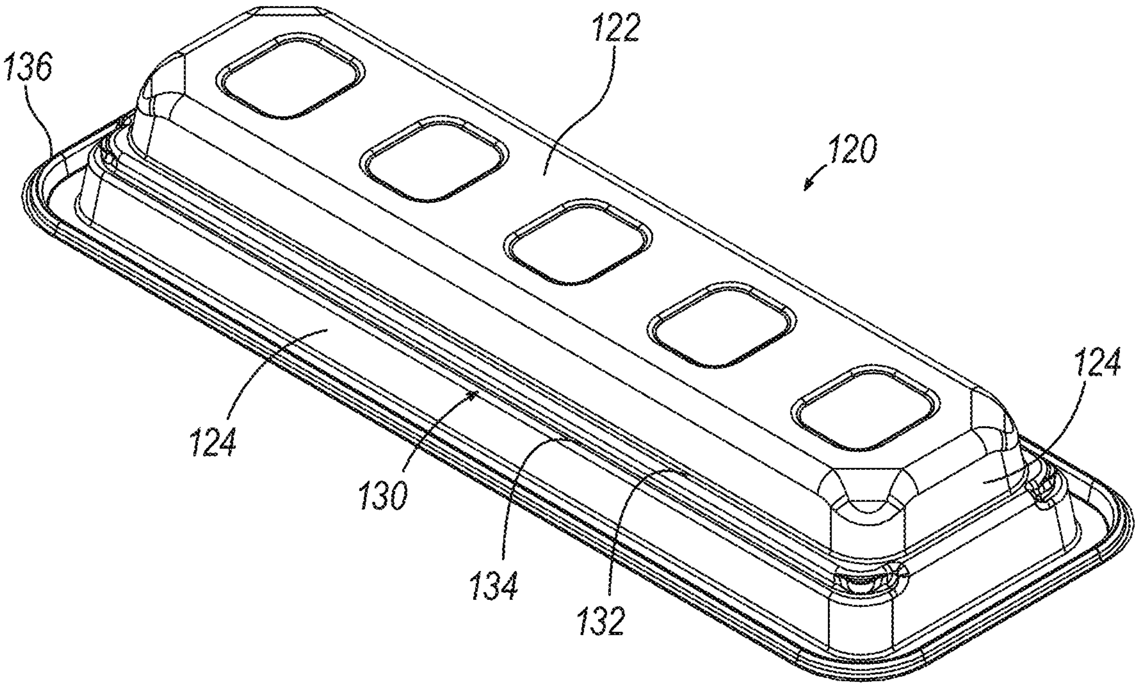
FIG. 3 depicts a bottom perspective view of a container tray of the packaging assembly of FIG. 1.

As best seen in FIGS. 2 and 3, container tray (120) is generally configured for the receipt of one or more components associated with a biopsy procedure. As will be described in greater detail below, container tray (120) and retainer tray (140) may operate cooperatively to contain such components for the purpose of initial sterilization and to maintain sterilization until use. Thus, container tray (120) may include thin and lightweight materials with some durability to withstand impacts during transportation and/or stresses from certain modes of sterilization such as beta or gamma radiation, ethylene oxide, or steam.

Container tray (120) in the present version includes a floor (122) and sidewalls (124) extending upwardly from floor (122). Sidewalls (124) and floor (122) together define an open upper portion (126) and inner interior space (128) configured to receive a biopsy device and other associated components, as will be described in greater detail below. Although the combination of floor (122) and sidewalls (124) may take on a variety of forms, the present version has a generally rectangular shape with rounded corners that generally corresponds to the footprint of a biopsy device and other associated components.

Each sidewall (124) extends upwardly from floor (122) at an outwardly extending angle such that inner interior space (128) expands in area further away from floor (122). In other words, sidewalls (124) generally form a tapered shape. In some versions, such a tapered shape may be desirable to promote ease of use in removal of items from container tray (120). In other versions, such a tapered shape may be omitted, and sidewalls (124) may extend away from floor (122) at about a 90° angle.

Sidewalls (124) together define an intermediate step (130) and an upper lip (136). Intermediate step (130) is formed integrally with each sidewall (124) and defines an outwardly extending lower flat portion (132) and upper flat portion (134) generally extending around the perimeter of container tray (120). In the present version, lower flat portion (132) extends around the entire perimeter of container tray (120), while upper flat portion (134) blends into lower flat portion (132) at some points. Specifically, on opposite ends of container tray (120), upper flat portion (134) curves into lower flat portion (132) such that only lower flat portion (132) in a portion of each side of container tray (120). The present configuration of lower flat portion (132) and upper flat portion (134) may be desirable to promote grip of container tray (120) and may be reconfigured in some versions with both lower flat portion (132) and upper flat portion (134) extending entirely around the perimeter of container tray (120).

Intermediate step (130) along with each flat portion (132, 134) are generally positioned at about the center of each sidewall (124). As will be described in greater detail below, the particular position of each flat portion (132, 134) relative to floor (122) may be configured to correspond to elements of retainer tray (140) for both receipt of retainer tray (140) and use in other contexts besides containment of biopsy procedure components. Thus, both lower flat portion (132) and upper flat portion (134) are defined within both the interior of container tray (120) and the exterior of container tray (120). Although not shown, it should be understood that in some versions the geometry of lower flat portion (132) and/or upper flat portion (134) may be varied to provide an integral fastener within inner interior space (128) for retainer tray (140). Such an integral fastener may be configured to releasably engage retainer tray (140) to releasably couple retainer tray (140) to container tray (120)

Upper lip (136) extends outwardly from each sidewall (124) around the perimeter of an upper portion of container tray (120) to define the perimeter of open upper portion (126). Upper lip (136) is generally configured to provide a flat upper surface around open upper portion (126) to adhere sterile barrier (112) to. Additionally, upper lip (136) may provide a gripping surface in some versions to promote manipulation of container tray (120). Accordingly, in some versions, upper lip (136) itself may include a downwardly extending flange, lip, or surface to facilitate improved grip.

Although not shown, it should be understood that in some versions, container tray (120) may include certain fixation features to hold components disposed within container tray (120) in a predetermined position. Such fixation features may be integral with floor (122) and/or sidewalls (124) and may include combinations of protrusions and/or indentations configured to receive specific elements of a given component. Additionally, such fixation features may include detents or other features to provide a detachable snap-fit coupling between container tray (120) and components configured for use with such fixation features.

Figure 4:
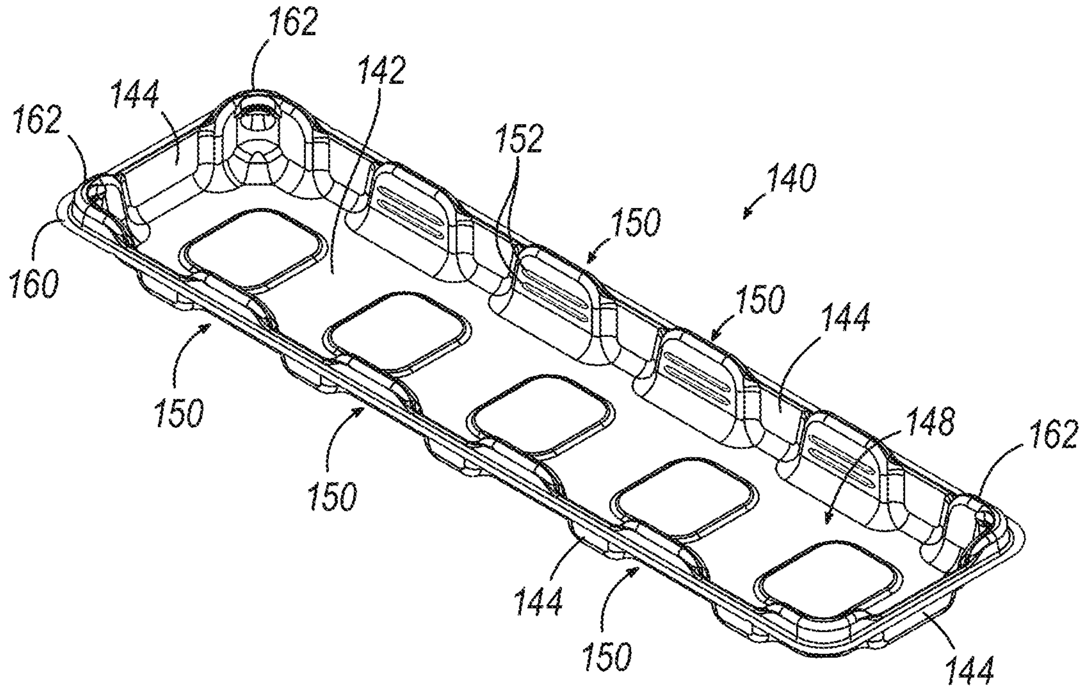
FIG. 4 depicts a perspective view of a retainer tray of the packaging assembly of FIG. 1.

Retainer tray (140) is shown in greater detail in FIG. 4. Retainer tray (140) is generally configured for receipt within container tray (120) to fully enclose biopsy procedure components between container tray (120) and retainer tray (140). Additionally, as will be described in greater detail below, retainer tray (140) is generally configured for use during a biopsy procedure as a sterile work surface for components associated with the biopsy procedure. Thus, retainer tray (140) may include a dual-use functionality where retainer tray (140) is used to contain biopsy procedure components or as a work surface for components associated with a biopsy procedure.

Retainer tray (140) in the present version includes a floor (142) and sidewalls (144) extending upwardly from floor (142). Sidewalls (144) and floor (142) together define an inner interior space (148) that is open to the exterior of retainer tray (140). Interior space (148) is generally configured to receive one or more biopsy procedure components, as will be described in greater detail below.

The particular shape of retainer tray (140) defined by floor (142) and sidewalls (144) is generally rectangular in the present version. Although a variety of shapes may be used in other versions, it may be generally desirable for the shape used for retainer tray (140) to correspond to the shape of container tray (120). As will be described in greater detail below, such a correspondence in shape may permit retainer tray (140) to nest within container tray (120). The size or footprint of retainer tray (140) may thus be sized to correspond to various features of container tray (120) to thereby permit retainer tray (140) to rest within container tray (120) on such features.

Each sidewall (144) extends upwardly from floor (142) at an outwardly extending angle such that inner interior space (148) expands in area further away from floor (142). In other words, sidewalls (144) generally form a tapered shape. In some versions, such a tapered shape may be desirable to promote ease of use in removal of retainer tray (140) from container tray (120). In other versions, such a tapered shape may be omitted, and sidewalls (144) may extend away from floor (142) at about a 90° angle.

One or more of each sidewall (144) defines one or more grasping features (150). In the present versions, grasping features (150) are defined by two sidewalls (144) on opposing sides of retainer tray (140). Specifically, each sidewall (144) defining grasping features (150) includes a plurality of grasping features (150). In the present version, the particular number of grasping features (150) per side defined by each sidewall (144) is four, although in other versions, five, two, one, or etc. may be defined by each sidewall (144).

Each gasping feature (150) is generally configured as a square or rectangular indentation in the outer surface of retainer tray (140). As will be described in greater detail below, the particular size and shape of each grasping feature (150) is generally configured to receive one or more fingers such that retainer tray (140) may be grasped by an operator even when retainer tray (140) is disposed within container tray (120). To further facilitate grip, each gasping feature (150) includes one or more outwardly projecting ribs (152) to provide a more irregular surface. Although the present version includes ribs (152) to facilitate enhanced grip, it should be understood that various alternative structures may be used in other versions such as outwardly or inwardly extending bumps, rough surface treatments, and/or high friction coatings.

Sidewalls (144) further include a retainer lip (160) extending around the perimeter of retainer tray (140). Retainer lip (160) extends outwardly from each sidewall (144) about orthogonally relative to each sidewall (144). In other words, retainer lip (160) may extend directly outwardly from each sidewall (144).

Retainer lip (160) is generally configured to engage a portion of container tray (120) to facilitate nesting of retainer tray (140) within container tray (120). For instance, in the present version, retainer lip (160) is configured to engage upper flat portion (134) within interior space (128) of container tray (120), as will be described in greater detail below. Additionally, in contexts where retainer tray (140) is used to provide a sterile working surface, retainer lip (160) may be configured to engage other components to hold retainer tray (140) in a predetermined position.

In the present version, each grasping feature (150) extends upwardly (relative to the view shown in FIG. 4) within interior space (148) to extend upwardly relative to retainer lip (160). In this configuration, gasping features (150) may provide an additional engagement surface for engagement with container tray (120). In particular, and as will be described in greater detail below, grasping features (150) may engage lower flat portion (132) within interior space (128) of container tray (120), while retainer lip (160) may engage upper flat portion (134) within interior space (128) of container tray (120). Of course, in other versions, such an upward extension of one, more, or all of grasping features (150) may be omitted and only retainer lip (160) may engage container tray (120).

Retainer tray (140) further includes a plurality of locators (162) disposed at each corner of retainer tray (140). Locators (162) in the present version define a similar profile to the upward extension of each grasping feature (150) described above. In particular, each locator (162) extends upwardly (relative to the view shown in FIG. 4) away from retainer lip (160). As will be described in greater detail below, each locator (162) is configured to engage a portion of container tray (120) such as lower flat portion (132) and/or upper flat portion (134) to promote nesting of retainer tray (140) within container tray (120). Although the present version includes four locators (162) of a generally rounded configuration, it should be understood that in other versions various alternative numbers and/or configurations of locators (162) may be used. In yet other versions, locators (162) may be omitted entirely.

Although not shown, it should be understood that in some versions, retainer tray (140) may include certain fixation features to hold components disposed within retainer tray (140) in a predetermined position. Such fixation features may be integral with floor (142) and/or sidewalls (144) and may include combinations of protrusions and/or indentations configured to receive specific elements of a given component. Additionally, such fixation features may include detents or other features to provide a detachable snap-fit coupling between retainer tray (140) and components configured for use with such fixation features.

Figure 5:
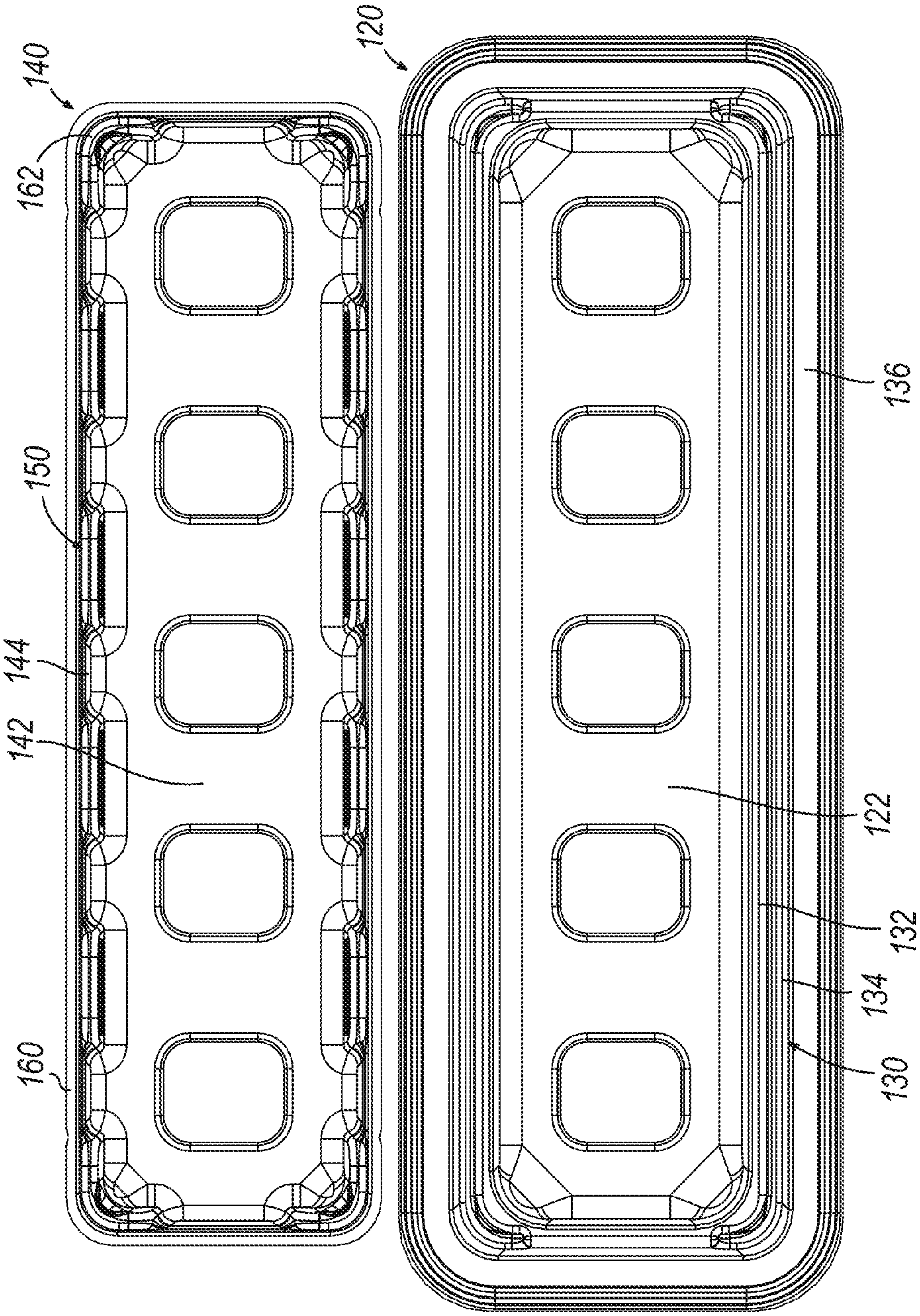
FIG. 5 depicts a top plan view of the container tray of FIG. 3 and the retainer tray of FIG. 4, the container tray and retainer tray being in a side-by-side configuration.

FIG. 5 shows container tray (120) and retainer tray (140) in a side-by-side configuration for footprint comparison purposes. As can be seen, the footprint of container tray (120) is generally larger relative to retainer tray (140) so that retainer tray (140) may be received within a portion of container tray (120). Yet, a portion of the footprint of container tray (120) corresponds to the footprint of retainer tray (140). In particular, the footprint defined by intermediate step (130) of container tray (120) generally corresponds to the footprint defined by retainer tray (140). This correspondence in footprints promotes nesting of retainer tray (140) within container tray (120). As will be understood, retainer tray (140) may be received within container tray (120), but only to a particular depth defined by intermediate step (130). Retainer tray (140) may then rest upon intermediate step (130) so that certain biopsy procedure components may be contained between retainer tray (140) and container tray (120).

The footprint correspondence described above may also be configured to promote use of retainer tray (140) and container tray (140) in other contexts besides nesting contexts. For instance, and as will be described in greater detail below, retainer lip (160) of retainer tray (140) and intermediate step (130) of container tray (120) generally defines a substantially similar outer profile and/or outer footprint. This substantially similar characteristic of retainer tray (140) and container tray (120) may be used so that both retainer tray (140) and container tray (120) may be received in a common receiving feature or features during a biopsy procedure. Such a common receiving feature or features will be described in greater detail below.

Figure 6:
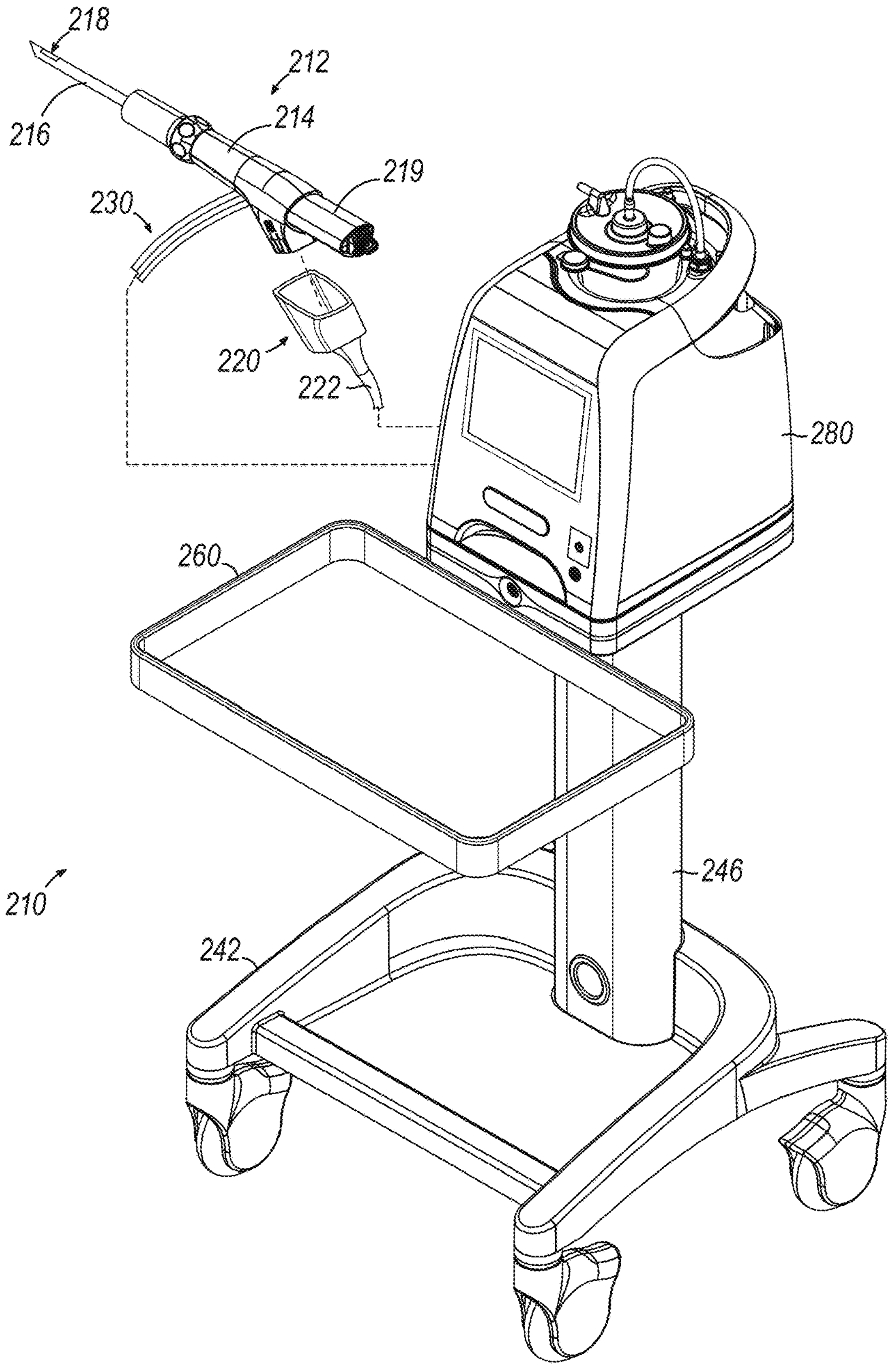
FIG. 6 depicts a perspective view of an example of a biopsy system for use with the packaging assembly of FIG. 1.

As described above, packaging assembly (110) may be used with certain biopsy procedure components during and prior to a biopsy procedure. As best seen in FIG. 6, packaging assembly (110) may be used with components of a biopsy system (210) both before and during a biopsy procedure. Biopsy system (210) includes a biopsy probe (212), a holster (220), a tube set (230), and a control module cart (240). Prior to a biopsy procedure, packaging assembly (110) may be used to contain biopsy probe (212) and tube set (230) of biopsy system (210) (see FIG. 2). Biopsy probe (212) is a disposable component that may be coupled to a reusable holster (220) for use during a biopsy procedure to collect one or more tissue samples. When biopsy probe (212) and holster (220) are coupled together, they may collectively be referred to as a biopsy device. Due to the nature of biopsy probe (212) being disposable and holster (220) being reusable, sterilization of such components may occur separately. Thus, biopsy probe (212) may be sterilized within packaging assembly (110) at the manufacturer and contained therein until a biopsy procedure, while holster (220) may be sterilized separately using clinical sterilization equipment in the field.

Biopsy probe (212) includes a body (214) with needle (216) extending from body (214) and a cutter (not shown). The cutter may be translatable within the needle (216) relative to a lateral aperture (218) for severing of one or more tissue samples. Such severed tissue samples may then be collected or stored within a tissue sample holder (219) coupled to body (214).

Holster (220) may detachably couple to biopsy probe (212) to provide power for one or more functions of biopsy probe (212). For instance, holster (220) includes a cable (222), which may be coupled to a power source included within control module cart (240). Cable (222) may be configured to communicate power to a portion of holster (220) so that such power may be ultimately communicated to biopsy probe (212) to power functions of biopsy probe (212) like rotation and/or translation of the cutter.

Tube set (230) includes one or more tubes that are configured to communicate fluids to biopsy probe (212). In particular, tube set (230) may extend from biopsy probe (212) and couple to one or more portions of control module cart (240). As will be described in greater detail below, one or more components of control module cart (240) may be configured to communicate various fluids to biopsy probe (212) via tube set (230). For instance, in some versions, tube set (230) may communicate vacuum to biopsy probe (212). In addition, or in the alternative, tube set (230) may communicate saline, meds, or other therapeutic mediums to biopsy probe (212). Like with biopsy probe (212) described above, tube set (230) is also disposable. Tube set (230) may therefore also be contained within packing assembly (110) prior to a biopsy procedure for sterilization purposes.

Control module cart (240) includes a base (242), a post (246) extending upwardly from base (242), a support member (260) (also referred to as a support ring), and a control module (280). Base (242) in the present version is configured as a wheeled base, although in other versions, base (242) may be of any other suitable configuration to provide stability to post (246) for support of control module (280) and support member (260).

Support member (260) is secured to at least a portion of post (246) proximate an upper portion of post (246). As will be described in greater detail below, support member (260) is generally configured to hold elements of packaging assembly (110) in a position about waist height for use by an operator during a biopsy procedure. Support member (260) in the present version is configured as a rigid strip of material that bends in four corners to form a rectangular ring-shape, hoop-shape, or box-shape. Thus, the central portion of support member (260) is open.

Although support member (260) forms a generally rectangular shape, it should be understood that in other versions, support member (260) may define a variety of alternative shapes. For instance, in some versions, support member (260) may define an L-shape, a cross-shape, a triangular shape, or etc. As will be understood, the particular shape of support member (260) generally corresponds to the shape of elements of packaging assembly (110). Thus, in versions with alternative shapes for support member (260), such alternative shapes may correspond to alternative shapes of elements of packaging assembly (110). In addition, or in the alternative, such alternative shapes may be configured to accommodate additional elements of packing assembly (110) and/or additional packaging assemblies (110) entirely.

Control module (280) is secured to a top portion of post (246) such that control module (280) may be generally accessible to an operator. Control module (280) is generally configured to support one or more functions of biopsy probe (212). For instance, control module (280) may include motors, power sources, fluid reservoirs, and/or various circuitry to generate vacuum or otherwise manipulate fluid for communication to or from biopsy probe (212). To facilitate operation of such components, control module (280) may further include various user interface features such as a touch screen, buttons, and/or etc.

In some versions, control module (280) may additionally control operation of holster (220). For instance, control module (280) may include electrical circuitry configured to communicate electrical signals configured to drive motors within holster (220) itself or within control module (280) to ultimately control the functionality of holster (220), which may ultimately control functions of biopsy probe (212). To facilitate operation of such components, control module (280) may similarly include various user interface features such as a touch screen, buttons, and/or etc.

Although components of biopsy system (210) are shown and described herein as having certain specific configurations and features, it should be understood that in other versions, packaging assembly (110) may be used with a variety of biopsy systems (210). In some versions, biopsy system (210) may be configured in accordance with any one or more of the teachings of U.S. Pat. No. 5,526,822, entitled "Method and Apparatus for Automated Biopsy and Collection of Soft Tissue," issued Jun. 18, 1996; U.S. Pat. No. 6,017,316, entitled "Vacuum Control System and Method for Automated Biopsy Device," issued Jan. 25, 2000; U.S. Pat. No. 6,086,544, entitled "Control Apparatus for an Automated Surgical Biopsy Device," issued Jul. 11, 2000; U.S. Pat. No. 6,162,187, entitled "Fluid Collection Apparatus for a Surgical Device," issued Dec. 19, 2000; U.S. Pat. No. 7,442,171, entitled "Remote Thumbwheel for a Surgical Biopsy Device," issued Oct. 8, 2008; U.S. Pat. No. 7,938,786, entitled "Vacuum Timing Algorithm for Biopsy Device," issued May 10, 2011; U.S. Pat. No. 8,118,755, entitled "Biopsy Sample Storage," issued Feb. 1, 2012; U.S. Pat. No. 8,532,747, entitled "Biopsy Marker Delivery Device," issued Sep. 10, 2013; U.S. Pat. No. 8,764,680, entitled "Handheld Biopsy Device with Needle Firing," issued on Jun. 11, 2014; U.S. Pat. No. 8,858,465, entitled "Biopsy Device with Motorized Needle Firing," issued Oct. 14, 2014; U.S. Pat. No. 9,326,755, entitled "Biopsy Device Tissue Sample Holder with Bulk Chamber and Pathology Chamber," issued May 3, 2016; and U.S. Pat. No. 9,486,186, entitled "Biopsy Device With Slide-In Probe," issued Nov. 8, 2016. The disclosure of each of the above-cited U.S. Patents is incorporated by reference herein.

Figure 7A:
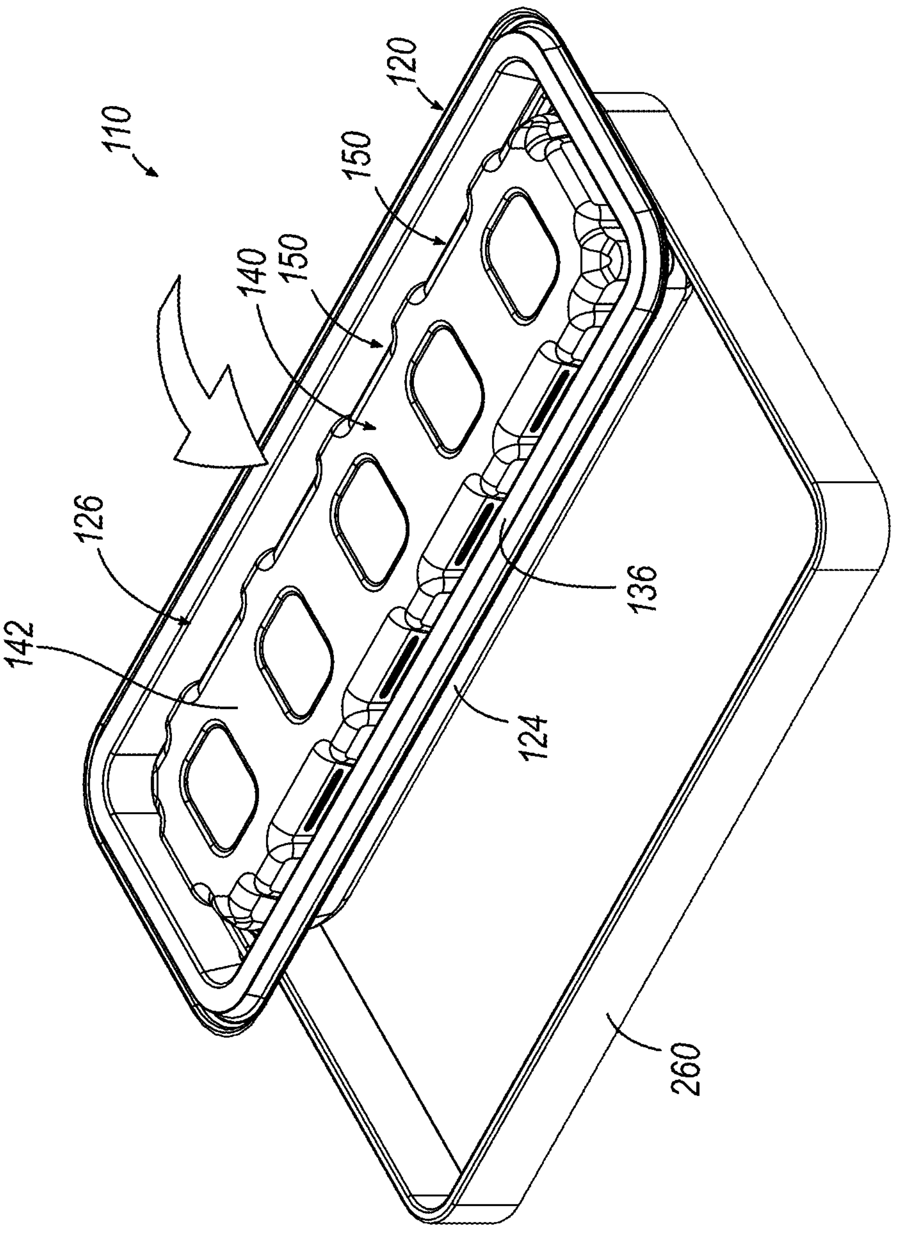
FIG. 7A depicts a perspective view of the packing assembly of FIG. 1 in use with the biopsy system of FIG. 6, the container tray of FIG. 3 being disposed in a support member of the biopsy system.
Figure 7B:
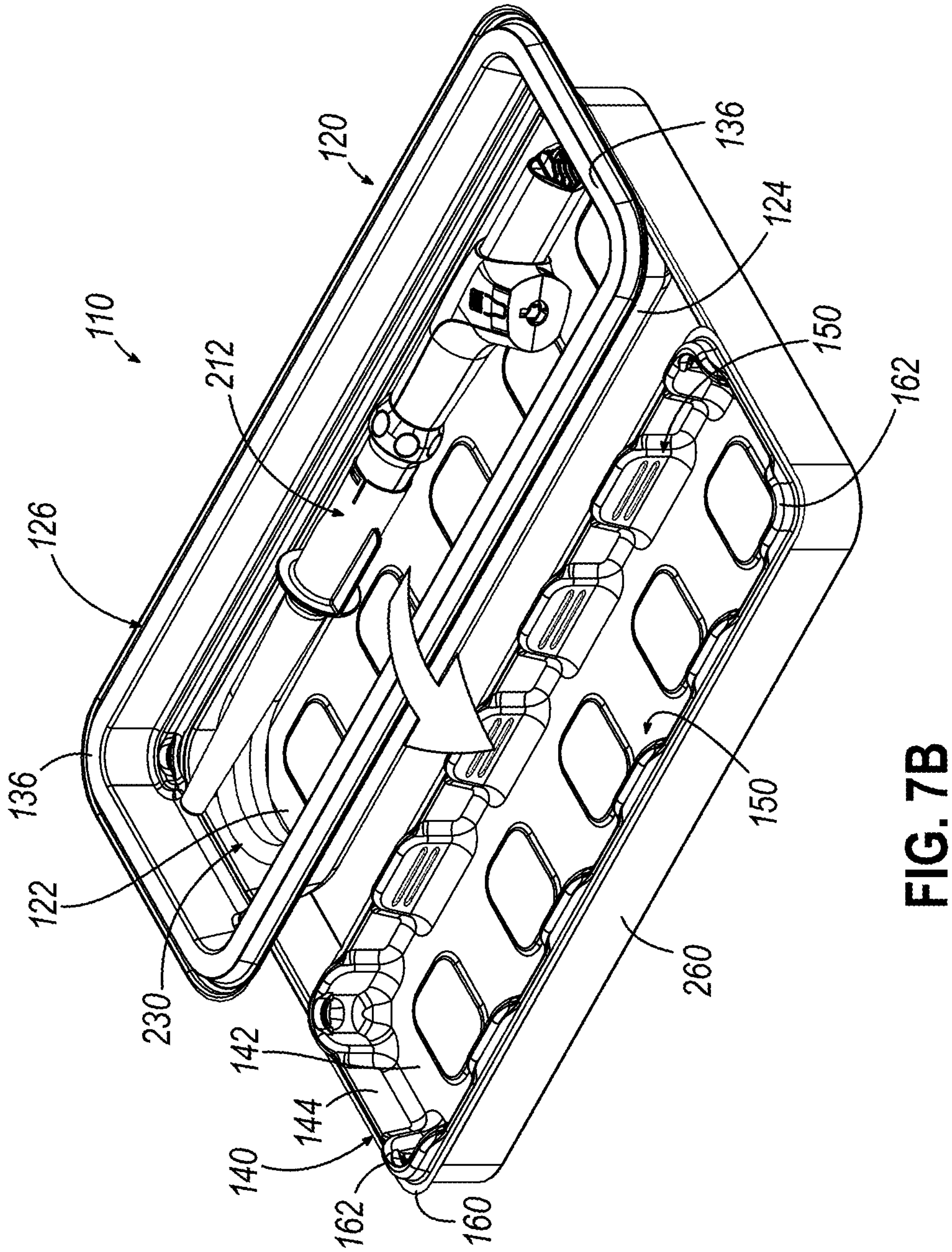
FIG. 7B depicts another perspective view of the packing assembly of FIG. 1 in use with the biopsy system of FIG. 6, the retainer tray of FIG. 4 being removed from the container tray of FIG. 3 and disposed in the support member of FIG. 7A.

FIGS. 1, 7A and 7B show an example of a use of packaging assembly (110) in combination with biopsy system (210). Packaging assembly (110) may initially begin as a fully contained assembly with biopsy probe (212) and tube set (230) disposed between container tray (120) and retainer tray (140). Additionally, sterile barrier (112) may be fully secured to upper lip (136) of container tray (120) to maintain sterility of the interior of container tray (120) during handling of packing assembly (110) prior to a biopsy procedure. In this initial configuration, packaging assembly (110) along with biopsy probe (212) and tube set (230) may be sterilized using one or more sterilization techniques. In some versions, sterilization may occur at the manufacturer, although sterilization may alternatively occur in a variety of other locations.

In preparation for a biopsy procedure, sterile barrier (112) may be removed from container tray (120). As shown in FIG. 1, sterile barrier (112) may be peeled away from upper lip (136) to expose the interior of container tray (120). Once sterile barrier (112) is fully removed, retainer tray (140) may be exposed for access to biopsy probe (212) and tube set (230).

After removal of sterile barrier (112), container tray (120) may be placed onto support member (260) of control module cart (240) as shown in FIG. 7A. In this configuration, intermediate step (130) of container tray (120) may rest on support member (260) with sidewalls (124) extending through the open interior portion of support member (260) such that floor (122) may be disposed beneath support member (260). In the present version, lower flat portion (132) is configured to rest on support member (260), although in other versions, any other suitable portion of intermediate step (130) may be configured to rest on support member (260).

Once container tray (120) is placed on support member (260), retainer tray (140) may be removed from container tray (120) to expose biopsy probe (212) and tube set (230). In particular, an operator may grasp one or more of grasping features (150) to lift retainer tray (140) from container tray (120). Due to the particular configuration of grasping features (150) an operator may grip retainer tray (140) by only grasping the exterior of retainer tray (140), thereby preserving sterility of the interior of retainer tray (140).

Once retainer tray (140) is removed from container tray (120), an operator may flip retainer tray (140) to orient retainer lip (160) facing upwardly to the position shown in FIG. 7B. During this flipping motion, an operator may maintain grip on gasping features (150) to grasp only the exterior of retainer tray (140), again preserving sterility of the interior of retainer tray (140).

Once retainer tray (140) is flipped, retainer tray (140) may be placed into support member (260) of control module cart (240) as shown in FIG. 7B. In the present configuration, support member (260) is configured to receive retainer tray (140) adjacent to container tray (120) with retainer tray (140) and container tray (120) in a side-by-side configuration. In other versions, support member (260) may be configured to receive retainer tray (140) and container tray (120) in a variety of other configurations. As described above, the footprint of retainer lip (160) of retainer tray (140) generally corresponds to the footprint of intermediate step (130) of container tray (120). Retainer tray (140) may thus rest on support member (260) via retainer lip (160) as similarly described above with respect to intermediate step (130).

Once retainer tray (140) is disposed on support member (260), biopsy probe (212) and tube set (230) may be removed from container tray (120) and connected to other components of biopsy system (210) in preparation for a biopsy procedure. Retainer tray (140) may then be used either before, during, or after a biopsy procedure as a sterile work surface to rest various components associated with the biopsy procedure. Any suitable component where maintenance of sterility is desired may be rested on retainer tray (140). By way of example only, some suitable components may include syringes, tip protectors, gauze, dressings, sutures, forceps, tweezers, scalpels, and/or etc.

At the conclusion of a biopsy procedure, both retainer tray (140) and container tray (120) may then be disposed of into the medical waste stream. Such disposal may also include other disposable components such as biopsy probe (212), tube set (230), and/or other disposable components.

II. Example of Alternative Dual-Purpose Packaging

Figure 8:
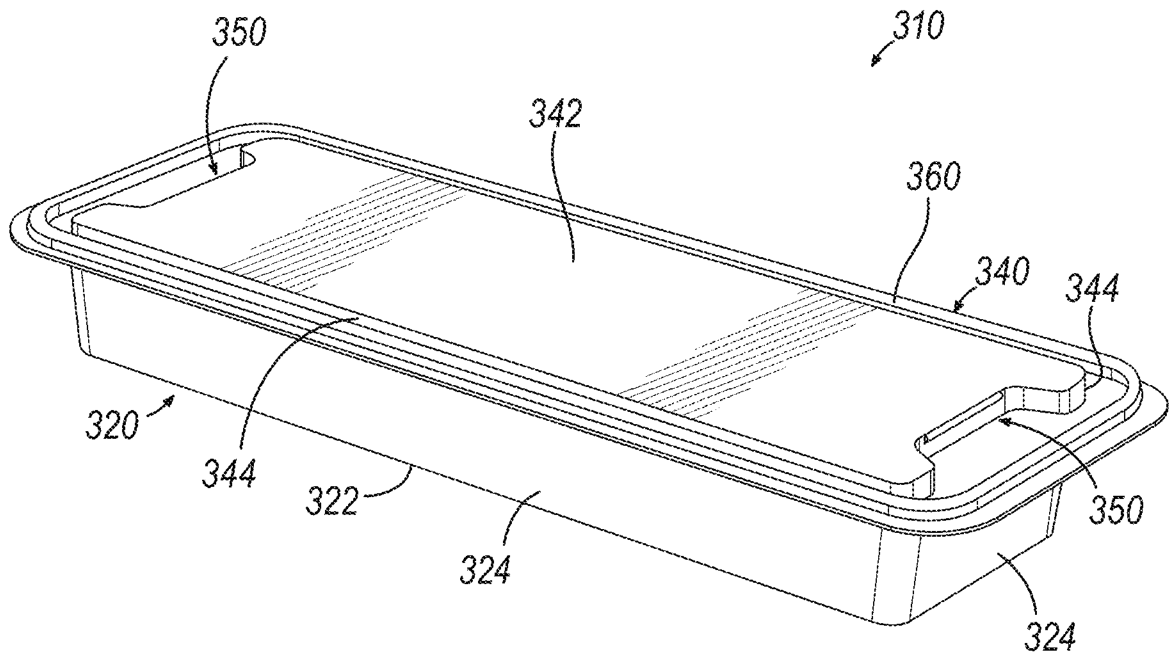
FIG. 8 depicts a perspective view of an example of an alternative sterile dual-purpose packaging assembly for use with the biopsy system of FIG. 6.

FIG. 8 shows an alternative packaging assembly (310) that may be used with biopsy system (210) as similarly described above with respect to packaging assembly (110) either in addition to, or in lieu of, packaging assembly (110). Packaging assembly (310) of the present version is substantially similar to packaging assembly (110) described above, unless otherwise noted herein. For instance, like packing assembly (110), packaging assembly (310) includes a container tray (320) and a retainer tray (340). As with container tray (120) and retainer tray (140) described above, container tray (320) and retainer tray (340) of the present version are generally configured to contain biopsy probe (212) and associated elements such as tube set (230) to maintain sterility of biopsy probe (212) and associated elements prior to a biopsy procedure.

Like container tray (120) described above, container tray (320) of the present version includes a floor (322) and sidewalls (324) that define an interior space (328) that is open to the upper portion of container tray (320). However, unlike container tray (120), container tray (320) of the present version includes relatively flat sidewalls (324) that extend upwardly from floor (322) in a generally uniform pattern. In other words, container tray (320) of the present version omits features similar to intermediate step (130).

Similar to sidewalls (124) described above, sidewalls (324) of the present version defines an upper lip (336) extending around the perimeter of the upper portion of container tray (320). As with upper lip (136) described above, upper lip (336) of the present example extends outwardly from sidewalls (324) about orthogonally to define a flat surface on the upper portion of container tray (320). However, unlike upper lip (136) described above, upper lip (336) of the present example may include an upwardly extending portion, protrusion, or rib extending around the perimeter of container tray (320). As will be described in greater detail below, such an upwardly extending portion of upper lip (336) may be configured to be received within a portion of retainer tray (340) to promote coupling and/sealing between container tray (320) and retainer tray (340).

Unlike container tray (120) described above, container tray (320) of the present example omits elements similar to sterile barrier (112). Instead, and as will be described in greater detail below, retainer tray (340) may couple directly to upper lip (336) of container tray (320), thereby obviating the need for elements similar to sterile barrier (112). Such an omission may be desirable in some versions to promote reduced waste during use of packaging assembly (310). Although the present version omits elements similar to sterile barrier (112), it should be understood that in some versions of packaging assembly (310), elements similar to sterile barrier (112) may be included. In such versions, features of sterile barrier (112) may be desirable to promote tampering resistance.

Like retainer tray (140) described above, retainer tray (340) of the present version includes a floor (342) and sidewalls (344) that define an interior space (348) that is open to an area of retainer tray (340) opposite floor (342). However, unlike retainer tray (140), retainer tray (340) of the present version includes relatively flat sidewalls (344) that extend away from floor (342) in a generally uniform pattern. Additionally, sidewalls (344) are relatively short in length relative to sidewalls (144) described above.

Also, as with retainer tray (140) described above, retainer tray (340) of the present version includes one or more gasping features (350). However, unlike grasping features (150) described above, grasping features (350) are not fully integrated into sidewalls (344). Instead, grasping features (350) are incorporated into both a portion of sidewalls (344) and a portion of floor (342). Specifically, each grasping feature (350) is primarily formed by a depression or inward extension of floor (342) into the interior space (348) of retainer tray (340). Additionally, each grasping feature (350) is positioned proximate to the sides of retainer tray (340). As a result, the depression of each grasping feature (350) is partially formed by an inward extension of the sidewall (344) associated with a given gasping feature (350).

Unlike retainer tray (140) described above, retainer tray (340) of the present version includes two grasping features (350) rather than eight. In this configuration, one grasping feature (350) is oriented on an opposite side of retainer tray (340) relative to the other grasping feature (350). Thus, an operator may grasp each side of retainer tray (340) by grasping floor (342) directly rather than grasping sidewalls (344) exclusively.

Unlike gasping features (150) described above, grasping features (350) in the present version omit ribs (152). Instead, grip may be facilitated by a horizontal indentation of each grasping feature (350). In other words, floor (342) may form an overhang over a portion of each grasping feature (350). Such an overhang may for a space within each gasping feature (350) that may be configured to receive one or more fingers of an operator such that the operator may grasp retainer tray (350). Although structures similar to ribs (152) are omitted in the present version, it should be understood that in some versions, similar structures may be incorporated into gasping features (350). Such structures may include one or more ribs, bumps, protrusions, indentations, high friction coatings, and/or etc.

Like retainer tray (140) described above, retainer tray (340) of the present example includes a retainer lip (360). Retainer lip (360) in the present version is similar to retainer lip (160) described above in that retainer lip (360) extends about orthogonally from each sidewall around the perimeter of retainer tray (340). However, unlike retainer lip (160) described above, retainer lip (360) of the present version is configured to engage upper lip (336) of container tray (320) to couple and/or seal retainer tray (340) to container tray (320).

As described above, upper lip (336) of container tray (320) may include an upwardly extending portion, protrusion, or rib configured to engage retainer lip (360) of retainer tray (340). Retainer lip (360) may thus include features complementary to the features of upper lip (336) to promote engagement between retainer lip (360) and upper lip (336). Because upper lip (336) includes protruding features, retainer lip (360) of the present version may thus include a channel indentation, or depression extending towards floor (342). Such a channel or depression may be configured to receive the corresponding protrusion or rib of upper lip (336). Although the present version includes a protrusion associated with upper lip (336) and an indentation associated with retainer lip (360), it should be understood that in other versions, the configuration may be reversed. Additionally, in yet other versions, other complementary features may be used instead of a protrusion/indentation.

Figure 9A:
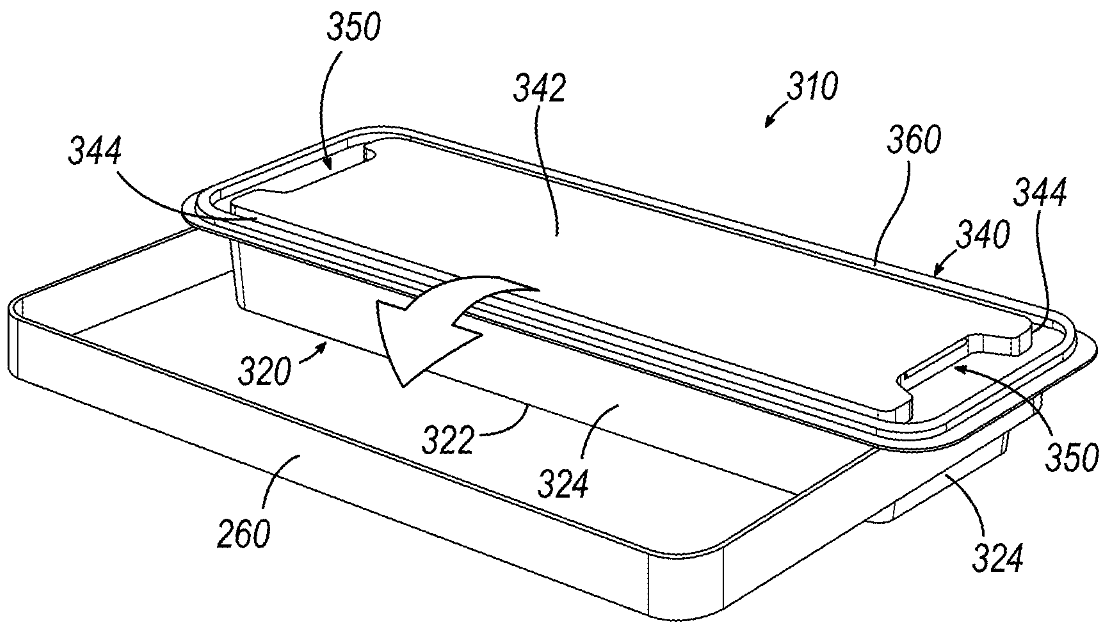
FIG. 9A depicts a perspective view of the packaging assembly of FIG. 8 in use with the biopsy system of FIG. 6, a container tray of the packaging assembly being disposed in the support member of FIG. 7A.
Figure 9B:
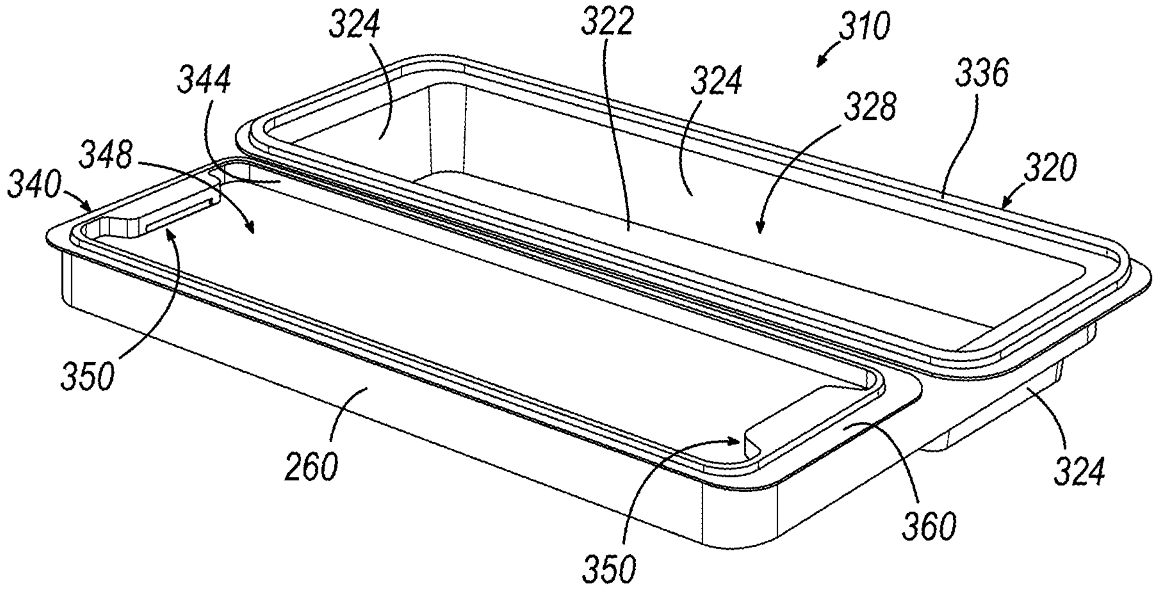
FIG. 9B depicts another perspective view of the packaging assembly of FIG. 8 in use with the biopsy system of FIG. 6, a retainer tray of the packaging assembly being removed from the container tray of FIG. 9A and disposed in the support member of FIG. 7A.

FIGS. 9A and 9B show an exemplary use of packaging assembly (310) in combination with biopsy system (210). As can be seen, retainer tray (340) may be initially coupled to container tray (320) to retain biopsy probe (212) and tube set (230) between retainer tray (340) and container tray (320). As described above with respect to packaging assembly (110), packaging assembly (310) may be sterilized along with components contained therein prior to beginning a biopsy procedure. Retainer tray (340) and container tray (320) may be then used to maintain sterility within the interior of packaging assembly (310) prior to a biopsy procedure.

During preparation for a biopsy procedure, the combination of retainer tray (340) and container tray (320) may be placed into support member (260) of control module cart (240). Container tray (320) may then rest on support member (260) via engagement between upper lip (336) and support member (260). Sidewalls (324) may then extend downwardly though the open interior of support member (260) such that floor (322) may be disposed below support member (260).

Once container tray (320) is engaged with support member (260), retainer tray (340) may be removed from container tray (320). Specifically, an operator may grasp each grasping feature (350) to pull retainer tray (340) from container tray (320). Due to the position of grasping features (350), retainer tray (340) may be manipulated without an operator having to touch interior space (348) of retainer tray (340). The sterility of interior space (348) of retainer tray (340) may thus be maintained as retainer tray (340) is manipulated.

Once retainer tray (340) is removed from container tray (320), retainer tray (340) may be flipped and placed upon support member (260) as shown in FIG. 9B. In this position, retainer lip (360) may engage support member (260) to hold retainer tray (340) in position on support member (260) adjacent to container tray (320) in a side-by-side configuration.

Once retainer tray (340) is disposed on support member (260), biopsy probe (212) and tube set (230) may be removed from container tray (320) and connected to other components of biopsy system (210) in preparation for a biopsy procedure. Retainer tray (340) may then be used either before, during, or after a biopsy procedure as a sterile work surface to rest various components associated with the biopsy procedure. Any suitable component where maintenance of sterility is desired may be rested on retainer tray (340). By way of example only, some suitable components may include syringes, tip protectors, gauze, dressings, sutures, forceps, tweezers, scalpels, and/or etc.

At the conclusion of a biopsy procedure, both retainer tray (340) and container tray (320) may then be disposed of into the medical waste stream. Such disposal may also include other disposable components such as biopsy probe (212), tube set (230), and/or other disposable components.

III. Exemplary of Multi-Container Dual-Purpose Packaging

Figure 10:
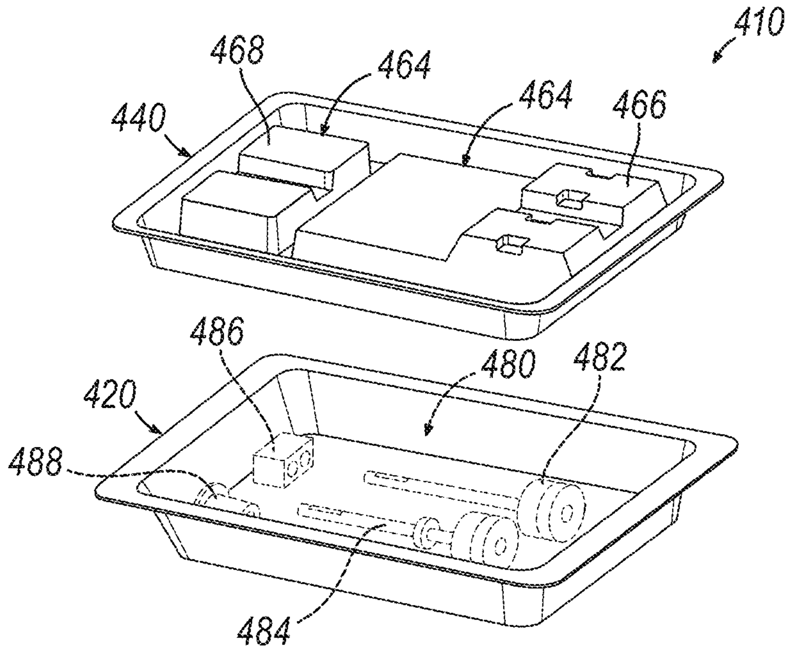
FIG. 10 depicts a perspective view of an example of a targeting set packaging assembly for use with the biopsy system of FIG. 6.
Figure 11:
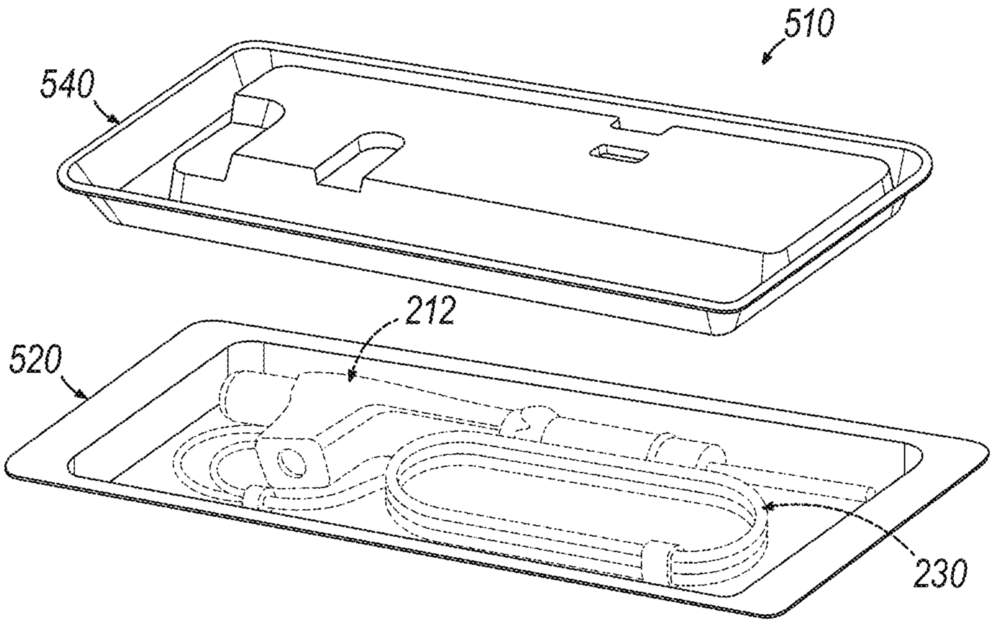
FIG. 11 depicts a perspective view of an example of a biopsy probe packaging assembly for use with the biopsy system of FIG. 6.

As noted above, in some uses of biopsy system (210) it may be desirable to use multiple sterile containers during a biopsy procedure. For instance, biopsy probe (212) may be packaged and sold separately from other accessory items. Thus, separate containers may be desirable for biopsy probe (212) and other associated accessory items. FIGS. 10 and 11 show an exemplary alternative multi-container packaging assembly that includes a targeting set packaging assembly (410) and a biopsy probe packaging assembly (510).

As shown in FIG. 10, targeting set packaging assembly (410) includes a container tray (420) and a retainer tray (440). Both container tray (420) and retainer tray (440) may be configured similarly to container trays (120, 320) and/or retainer trays (140, 340) described above. For instance, container tray (420) and retainer tray (440) may include features like one or more steps, lips, grasping features locators, interlocking channels/protrusions, and/or etc. Additionally, container tray (420) and retainer tray (440) may be configured to nest together to fully enclose certain components as will be described in greater detail below. Such a nesting feature may be used in some contexts to maintain the sterility within the interior of packaging assembly (410) until components container therein are used in connection with a biopsy procedure.

Unlike container trays (120, 320) and retainer trays (140, 340) described above, container tray (420) and retainer tray (440) may define a different size and/or shape to accommodate different components than biopsy probe (212) and tube set (230). For instance, in the present version, container tray (420) and retainer tray (440) are configured to together contain a targeting set (480). As will be described in greater detail below, targeting set (480) may occupy a different footprint and have greater separate components than the combination of biopsy probe (212) and tube set (230). Container tray (420) and retainer tray (440) may accordingly be sized as a smaller rectangular package in the present version to account for the different configuration of targeting set (480) relative to biopsy prove (212) and tube set (230).

Also unlike container trays (120, 320) and retainer trays (140, 340) described above, container tray (420) and retainer tray (440) may include certain fixation features configured to hold portions of targeting set (480) within a predetermined area in container tray (420) and/or retainer tray (440). For instance, as described above, targeting set (480) may include a plurality of separate components. It may therefore be desirable to hold these separate components in position within container tray (420) and retainer tray (440) to reduce movement of such components during transport of packaging assembly (410).

In the present version retainer tray (440) includes one or more fixation features (464) of integral construction with retainer tray (440). Although fixation features (464) are shown in the present version as only being associated with retainer tray (440), it should be understood that in other versions, fixation features (464) may be incorporated into container tray (420) only, or both container tray (420) and retainer tray (440).

Fixation features (464) include a targeting set fixation feature (466) and an accessory fixation feature (468). Both tarting set fixation feature (466) and accessory fixation feature (468) are configured to correspond to one or more features of different components of targeting set (480) as will be described in greater detail below. Thus, both targeting set fixation feature (466) and accessory fixation feature (468) may include a combination of indentations and protrusions to contour the inner surface of retainer tray (440) to certain features of targeting set (480). As a result, both targeting set fixation feature (466) and accessory fixation feature (468) may be configured to hold targeting set (480) in a predetermined position when retainer tray (440) is nested within container tray (420).

Targeting set (480) is generally configured for use in a magnetic resonance imaging (MRI) guided biopsy procedure. Targeting set (480) in the present example includes an obturator (482), a targeting cannula (484) configured to receive the obturator (482), a guide cube (486) configured to guide the combination of the obturator (482) and the targeting cannula (484), and one or more additional accessory items (488). In some versions, targeting set (480) may be constructed in accordance with one or more of the teachings of U.S. Pat. No. 9,504,453, entitled "MRI Biopsy Device," issued Nov. 29, 2016; U.S. Pat. No. 10,123,820, entitled "Grid and Rotatable Cube Guide Localization Fixture for Biopsy Device," issued Nov. 13, 2018; and U.S. Pat. No. 10,327,805, entitled "Biopsy Cannula Adjustable Depth Stop," issued Jun. 25, 2019, the disclosures of which are incorporated by referenced herein.

MRI equipment is prone to interference from metals such as metal used in needle (216) of biopsy probe (212). Thus, to reduce interference, targeting set (480) may be used initially to establish a position for biopsy probe (212) under MRI guidance. In this procedure, the combination of obturator (482) and targeting cannula (484) is first inserted into a patient using guide cube (486). Obturator (482) is configured to simulate the configuration of a biopsy needle, but without the use of metal. Thus, the position of obturator (482) is precisely set using MRI guidance. Once set, obturator (482) is removed from targeting cannula (484) and a biopsy needle is inserted while the MRI equipment is not in use. Packaging assembly (410) may therefore be desirable for contexts where MRI guidance is used to manage the additional components associated with MRI guided biopsy procedures.

As shown in FIG. 11, biopsy probe packaging assembly (510) includes a container tray (520) and a retainer tray (540). Both container tray (520) and retainer tray (540) may be configured similarly to container trays (120, 320) and/or retainer trays (140, 340) described above. For instance, container tray (520) and retainer tray (540) may include features like one or more steps, lips, grasping features locators, interlocking channels/protrusions, and/or etc. Additionally, container tray (520) and retainer tray (540) may be configured to nest together to fully enclose certain components as will be described in greater detail below. Such a nesting feature may be used in some contexts to maintain the sterility within the interior of packaging assembly (510) until components container therein are used in connection with a biopsy procedure.

Like container trays (120, 320) and retainer trays (140, 340) described above, container tray (520) and retainer tray (540) are generally configured to contain biopsy probe (212) and tube set (230). Thus, the footprint of container tray (520) and retainer tray (540) is generally substantially similar to the footprint of container trays (120, 320) and retainer trays (140, 340) described above.

Although not shown, it should be understood that in some versions, container tray (520) and retainer tray (540) may include certain fixation features configured to hold portions of biopsy probe (212) and/or tube set (230) within a predetermined area in container tray (520) and/or retainer tray (540). Such fixation features may be configured similarly to fixation features (464) described above, but with different shapes or configurations to account for the particular geometry of biopsy probe (212) and/or tube set (230).

Figure 12A:
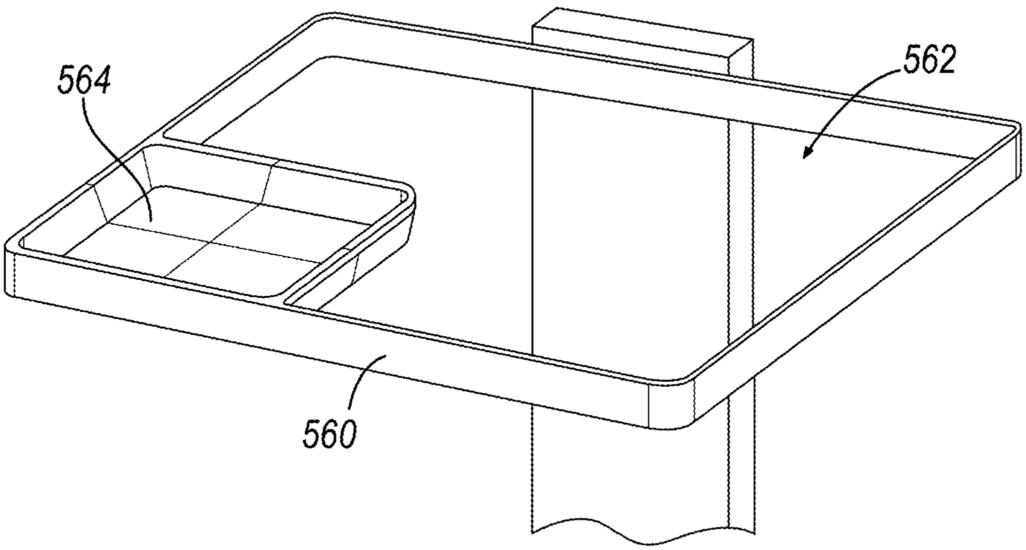
FIG. 12A depicts a perspective view of an example of an alternative support member that may be incorporated into the biopsy system of FIG. 6.

FIG. 12A shows an exemplary alternative support member (560) that may be readily integrated into biopsy system (210) described above either in addition to or in lieu of support member (260). Support member (560) is generally configured for use with multi-container packaging assemblies such as the combination of targeting set packaging assembly (410) and biopsy probe packaging assembly (510). Support member (560) is similar to support member (260) described above in that support member (560) includes a rigid elongate strip bent or curved into a generally square or rectangular pattern that defines an open inner area (562).

Unlike support member (260) described above, support member (560) of the present example defines a specific shape for the purpose of receiving portions of both targeting set packaging assembly (410) and biopsy probe packaging assembly (510). In particular, support member (560) in the present version includes an integral tray (564) disposed in one corner of the generally square or rectangular pattern defined by support member (560).

Although the term "integral" is used herein with respect to integral tray (564), it should be understood that in other versions, integral tray (564) need not be permanently affixed to, or of integral construction with, support member (560). Thus, in some versions, integral tray (564) may be removably couplable to support member (560) to promote flexibility of support member (560). For instance, in some versions, integral tray (564) may be removable to define a footprint substantially similar to the one described above with respect to support member (220) for use with packaging assemblies (110, 310) described above. In other contexts, integral tray (564) may be added for use in combination with targeting set packaging assembly (410) and biopsy probe packaging assembly (510) as described in greater detail below. Therefore, in some circumstances, integral tray (564) may simply be referred to as a detachable tray or an insert.

Integral tray (564) reduces the footprint of open inner area (562) such that open inner area (562) defines an L-shaped or J-shaped configuration. In this configuration, a portion of open inner area (562) is configured to receive a portion of targeting set packaging assembly (410), while another portion of open inner area (562) is configured to receive a portion of biopsy probe packaging assembly (510).

Figure 12B:
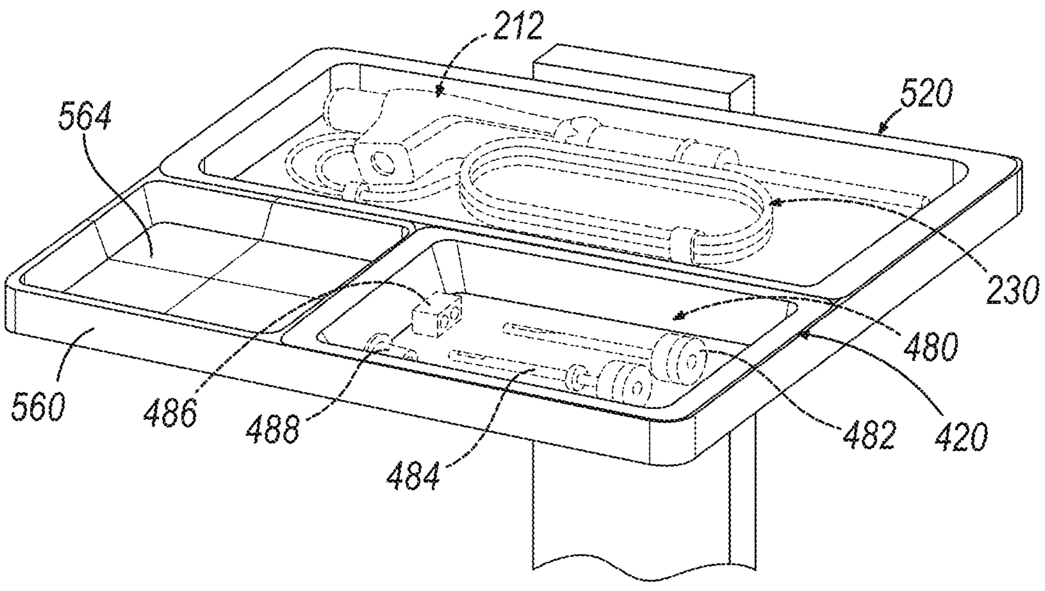
FIG. 12B depicts a perspective view of the targeting set packaging assembly of FIG. 10 and the biopsy probe packaging assembly of FIG. 11 in use with the support member of FIG. 12A.

FIGS. 12A and 12B show an exemplary use of targeting set packaging assembly (410) and biopsy probe packaging assembly (510) in combination with support member (560). As can be seen, support member (560) is initially open. At this point, retainer tray (440, 540) may be removed from each container tray (420, 520), respectively.

One each retainer tray (440, 540) is removed, each container tray (420, 520) may be placed into open inner area (562) of support member (560) as shown in FIG. 12B. Both container trays (420, 520) may then be used as a sterile work surface during the biopsy procedure for biopsy probe (212), tube set (230), targeting set (480), or other sterile components associated with a biopsy procedure. Optionally, at any point during the biopsy procedure, one or more of container trays (420, 520) may be converted to a non-sterile work surface at the discretion of an operator.

At the conclusion of the biopsy procedure, both retainer trays (440, 540) and container trays (420, 520) may then be disposed of into the medical waste stream. Such disposal may also include other disposable components such as biopsy probe (212), tube set (230), and/or other disposable components.

IV. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A system for maintaining sterility during a biopsy procedure, the system comprising: a cart, the cart including a support member defining an open inner portion and an opening in communication with the open inner portion; a packaging assembly having a container tray and a retainer tray; and a biopsy probe, the packaging assembly being configured to receive the biopsy probe, the open inner portion of the support member being configured engage a portion of both the container tray and the retainer tray simultaneously to hold the container tray and the retainer tray within the open inner portion of the support member to thereby provide a sterile work surface during the biopsy procedure.

Example 2

The system of Example 1, the retainer tray being configured to nest within a portion of the container tray.

Example 3

The system of Examples 1 or 2, the container tray defining an intermediate step, the intermediate step being configured to engage a portion of the retainer tray and a portion of the support member.

Example 4

The system of Example 3, the intermediate step including a first flat portion and a second flat portion, the retainer tray being configured to engage both the first flat portion and the second flat portion simultaneously.

Example 5

The system of Example 4, the support member being configured to engage the first flat portion or the second flat portion, but not both simultaneously.

Example 6

The system of any of Examples 1 through 5, the retainer tray including a retainer lip, the retainer lip being configured to engage the support member to hold the retainer tray within the open inner portion of the support member.

Example 7

The system of any of Examples 1 through 6, the retainer tray including a floor, a plurality of sidewalls, and a plurality of grasping features, each grasping feature of the plurality of grasping features being defined by the floor or one or more sidewalls.

Example 8

The system of Example 7, each grasping feature of the plurality of grasping features being defined by an indentation in a sidewall of the plurality of sidewalls.

Example 9

The system of Example 7, each grasping feature of the plurality of grasping features being defined by an indentation in the floor.

Example 10

The system of Example 7, each grasping feature of the plurality of grasping features being defined by an indentation in the floor, the indentation in the floor defining an overhang of the floor over at least a portion of each gasping feature.

Example 11

The system of any of Examples 7 through 10, each grasping feature including a plurality of ribs, the plurality of ribs being configured to enhance the grip of an operator with respect to reach grasping feature.

Example 12

The system of any of Examples 1 through 11, the cart being a control module cart, the control module cart including a base, a post, and a control module, the support member and the control module being coupled to an upper portion of the post.

Example 13

The system of any of Examples 1 through 12, the system further comprising a tube set, the tube set being configured to communicate fluids between the biopsy probe and a portion of the cart, the packaging assembly being configured to receive the tube set.

Example 14

The system of any of Examples 1 through 13, the container tray or the retainer tray including one or more protrusions, the one or more protrusions being configured to anchor the biopsy probe in a predetermined location within the packaging assembly.

Example 15

The system of any of Examples 1 through 14, the packaging assembly further including a sterile barrier, the sterile barrier being removably coupled to an upper portion of the container tray.

Example 16

A system for maintaining sterility in connection with a biopsy procedure, the system comprising: a cart; a container having a first portion and a second portion, the second portion being configured to nest within a portion of the first portion; a biopsy device, the container being configured to receive a portion of the biopsy device between the first portion and the second portion; and a support ring coupled to a portion of the cart, the support ring being bent to form a predetermined shape corresponding to the first portion and the second portion of the container, the support ring being configured to support both the first portion and the second portion of the container during a biopsy procedure.

Example 17

The system of Example 16, the first portion of the container including a first lip, the second portion of the container including a second lip, the second lip being configured to engage the first lip to removably couple the second portion to the first portion.

Example 18

The system of Example 16, the first portion of the container including a stepped portion defining an outer flat and an inner flat, the outer flat being configured to engage the support ring, the inner flat being configured to engage a portion of the second portion when the second portion is nested within the first portion.

Example 19

The system of any of Examples 16 through 18, the support ring having a rigid strip bent to form a rectangular shape, the support ring including a support ring tray, the support ring tray being fixedly secured to a portion of the rigid strip.

Example 20

A method for providing a sterile work surface during a biopsy procedure, the method comprising: providing a sterile packing assembly having a container tray nested within a retainer tray; removing the retainer tray from the container tray by gasping one or more indentations on an outer surface of the retainer tray to expose a sterile internal surface of the retainer tray; placing the retainer tray into an open inner portion defined by a support member of a control module cart with the sterile internal surface oriented upwardly away from the support member; and using the sterile internal surface as the sterile work surface during the biopsy procedure.

Example 21

The method of Example 20, further comprising removing a biopsy probe from the container tray after the step of removing the retainer tray from the container tray.

Example 22

The method of Examples 20 or 21, the step of placing the retainer tray into the support member being performed while gasping the one or more indentations on the outer surface of the retainer tray.

Example 23

The method of any of Examples 20 through 22, further comprising disposing of the container tray and the retainer tray into a medical waste stream.

Example 24

The method of any of Examples 20 through 23, further comprising removing a sterile barrier from the container tray prior to the step of removing the retainer tray from the container tray.

Example 25

The method of any of Examples 20 through 24, further comprising sterilizing the sterile packaging assembly while the retainer tray is nested within the container tray.

V. Miscellaneous

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Embodiments of the present invention have application in conventional endoscopic and open surgical instrumentation as well as application in robotic-assisted surgery.

By way of example only, embodiments described herein may be processed before surgery. First, a new or used instrument may be obtained and if necessary cleaned. The instrument may then be sterilized. In one sterilization technique, the instrument is placed in a closed and sealed container. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta or gamma radiation, ethylene oxide, or steam.

Embodiments of the devices disclosed herein can be reconditioned for reuse after at least one use. Reconditioning may include any combination of the steps of disassembly of the device, followed by cleaning or replacement of particular pieces, and subsequent reassembly. In particular, embodiments of the devices disclosed herein may be disassembled, and any number of the particular pieces or parts of the devices may be selectively replaced or removed in any combination. Upon cleaning and/or replacement of particular parts, embodiments of the devices may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A system for maintaining sterility during a biopsy procedure, the system comprising:

(a) a cart, the cart including a support member defining an open inner portion and an opening in communication with the open inner portion;

(b) a packaging assembly having a container tray and a retainer tray; and (c) a biopsy probe, the packaging assembly being configured to receive the biopsy probe, the open inner portion of the support member being configured engage a portion of both the container tray and the retainer tray simultaneously to hold the container tray and the retainer tray within the open inner portion of the support member to thereby provide a sterile work surface during the biopsy procedure.

2. The system of claim 1, the retainer tray being configured to nest within a portion of the container tray.

3. The system of claim 1, the container tray defining an intermediate step, the intermediate step being configured to engage a portion of the retainer tray and a portion of the support member.

4. The system of claim 3, the intermediate step including a first flat portion and a second flat portion, the retainer tray being configured to engage both the first flat portion and the second flat portion simultaneously.

5. The system of claim 4, the support member being configured to engage the first flat portion or the second flat portion, but not both simultaneously.

6. The system of claim 1, the retainer tray including a retainer lip, the retainer lip being configured to engage the support member to hold the retainer tray within the open inner portion of the support member.

7. The system of claim 1, the retainer tray including a floor, a plurality of sidewalls, and a plurality of grasping features, each grasping feature of the plurality of grasping features being defined by the floor or one or more sidewalls.

8. The system of claim 7, each grasping feature of the plurality of grasping features being defined by an indentation in a sidewall of the plurality of sidewalls.

9. The system of claim 7, each grasping feature of the plurality of grasping features being defined by an indentation in the floor.

10. The system of claim 7, each grasping feature of the plurality of grasping features being defined by an indentation in the floor, the indentation in the floor defining an overhang of the floor over at least a portion of each gasping feature.

11. The system of claim 7, each grasping feature including a plurality of ribs, the plurality of ribs being configured to enhance the grip of an operator with respect to reach grasping feature.

12. The system of claim 1, the cart being a control module cart, the control module cart including a base, a post, and a control module, the support member and the control module being coupled to an upper portion of the post.

13. The system of claim 1, the system further comprising a tube set, the tube set being configured to communicate fluids between the biopsy probe and a portion of the cart, the packaging assembly being configured to receive the tube set.

14. The system of claim 1, the container tray or the retainer tray including one or more protrusions, the one or more protrusions being configured to anchor the biopsy probe in a predetermined location within the packaging assembly.

15. The system of claim 1, the packaging assembly further including a sterile barrier, the sterile barrier being removably coupled to an upper portion of the container tray.

16. A system for maintaining sterility in connection with a biopsy procedure, the system comprising:

(a) a cart;

(b) a container having a first portion and a second portion, the second portion being configured to nest within a portion of the first portion;

(c) a biopsy device, the container being configured to receive a portion of the biopsy device between the first portion and the second portion; and (d) a support ring coupled to a portion of the cart, the support ring being bent to form a predetermined shape corresponding to the first portion and the second portion of the container, the support ring being configured to support both the first portion and the second portion of the container during a biopsy procedure.

17. The system of claim 16, the first portion of the container including a first lip, the second portion of the container including a second lip, the second lip being configured to engage the first lip to removably couple the second portion to the first portion.

18. The system of claim 16, the first portion of the container including a stepped portion defining an outer flat and an inner flat, the outer flat being configured to engage the support ring, the inner flat being configured to engage a portion of the second portion when the second portion is nested within the first portion.

19. The system of claim 16, the support ring having a rigid strip bent to form a rectangular shape, the support ring including a support ring tray, the support ring tray being fixedly secured to a portion of the rigid strip.

* * * * *